Sept. 20, 1949. F. A. GODCHAUX Plant Pat. 873
CAMELLIA PLANT
Filed May 28, 1948
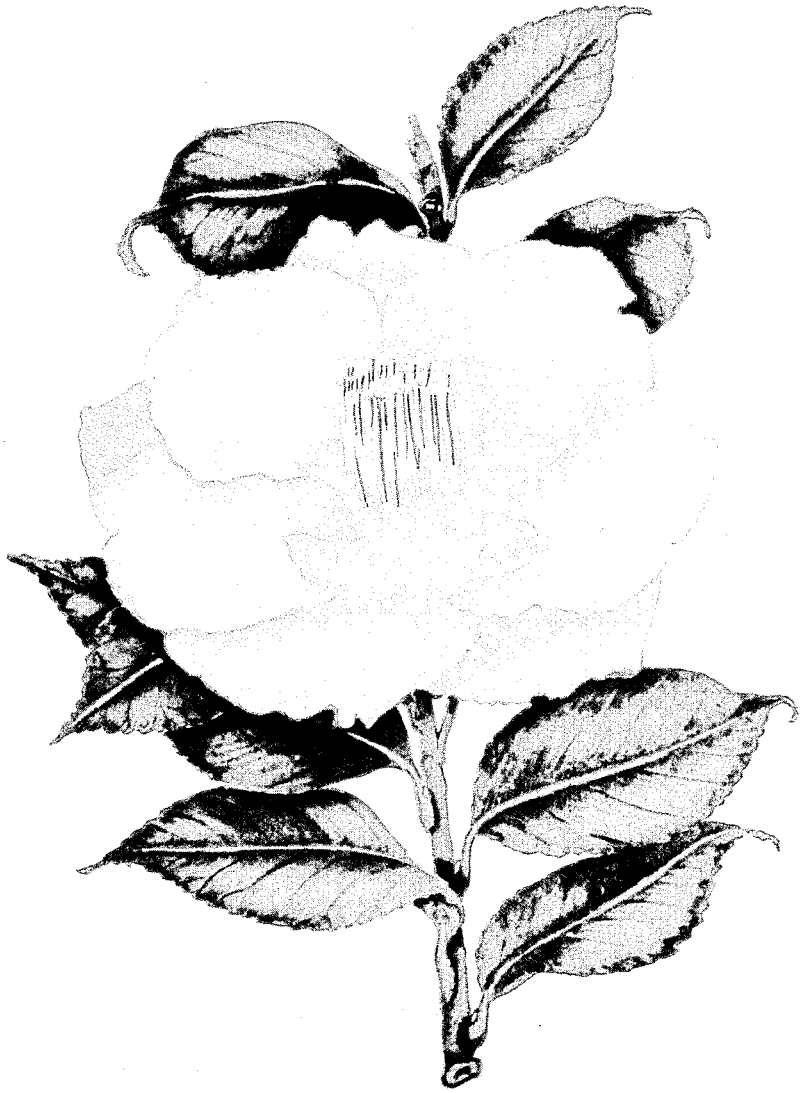
Inventor:
Frank A. Godchaux,
By: Pierce, Scheffler & Parker,
Attorneys.

Patented Sept. 20, 1949

Plant Pat. 873

UNITED STATES PATENT OFFICE

873

CAMELLIA PLANT

Frank A. Godchaux, Abbeville, La.

Application May 28, 1948, Serial No. 29,771

1 Claim. (Cl. 47—60)

This invention relates to a new and distinctive variety of camellia which may be generally designated as a semi-double variety having petals of a leathery texture, medium pink in color with white variegation in blotched or marbled patterns.

The parentage of the camellia is unknown, but it was produced from a group of seedlings planted by the applicant. The new and distinctive variety of camellia comprising the invention is characterized by the color and texture of the petals, showiness of the stamens and fragrance and other distinguishing features more particularly hereinafter described. In the description, for purpose of convenience and comparison the new camellia will be compared with the known variety, Empress.

The colors and characteristics of the new variety of camellia comprising the invention are indicated in the accompanying figure, which shows the fully opened camellia.

The texture of the petals of the flower is leathery and has a considerable amount of crimpling appearing on the upper surface of the top-most row of petals. This crepe-like appearance is variable in extent on individuals but is sufficient to set the new variety well apart from the well known variety, Empress, which is of the same general type.

The color of the petals is a clear medium pink close to Plate 41, J–1, as described in the Dictionary of Color, by A. Maerz and M. Rea Paul, published by McGraw Hill Book Company, Inc., New York, 1930 edition. In addition to the pink color, there is white variegation which may be in blotched or marbled patterns. The white variegations further set the new camellia apart from the variety, Empress.

The color of the base of the stamen is the same as the petals. The top two-thirds of the filament is white. The anthers are a bright yellow gold and very showy.

The stamens of which there are 84 to 116, depending on growing conditions, are more showy than on the variety, Empress. They form a larger cylinder than is formed on the variety, Empress.

Normally there are 9 to 10 sepals and 14 to 16 petals. Petaloids, when found, number from one to three. Petaloids normally appear in less than half of the blossoms.

The foliage and growth habit of the new camellia plant is different from the variety, Empress. The lateral buds can be distinctly seen. The leaf color is a rich green described as Wintergreen English Ivy and shown in Plate 23, A–12 in the Dictionary of Color, by A. Maerz and M. Rea Paul, referred to above. The leaf size is medium. The leaves have decidedly pointed tips, with slight serrations close to the petiole end and more pronounced but moderate serrations toward the opposite end. The general shape of the plant is somewhat more upright than Empress. It is densely branched and normally a vigorous grower.

The flower when fully open measures from 4¾ to 5¾ inches in diameter. It has considerable depth for a semidouble variety due to the fact that the petals have a tendency to curl. The new variety has a definite and distinctive fragrance which is lacking in most semi-double varieties.

The bloom dates may be said to be slightly earlier than mid-season. In the vicinity of Abbeville, La., blooms open in November, December and January. It is not uncommon for the plant to continue to bloom into February. While the new variety may be described as a floriferous one, it has no tendency to overload with flower buds. The flowers do not readily shed from the plant as is the case with variety, Empress.

The new variety of camellia plant has been asexually reproduced in the garden of the applicant at Abbeville, Louisiana, by grafting cuttings of the plant onto understock of *Camellia japonica* and *Camellia sasanqua*, using the usual cleft graft method.

I claim:

The new and distinct variety of camellia plant substantially as herein disclosed, characterized by the flower semi-double, medium pink variegated petals, with golden anthers on white filaments whose base is pink; fragrance definite, as compared to most semi-double varieties; rich green foliage and dense upright habit of growth.

FRANK A. GODCHAUX.

No references cited.